(12) United States Patent
Panditrao et al.

(10) Patent No.: US 7,842,847 B2
(45) Date of Patent: Nov. 30, 2010

(54) SEPARATION PROCESS FOR OLEFIN PRODUCTION

(75) Inventors: Sunil Panditrao, Hackettstown, NJ (US); Sanjeev Ram, Berkeley Heights, NJ (US)

(73) Assignee: Lummus Technology Inc., Bloomfield, NJ (US)

( * ) Notice: Subject to any disclaimer, the term of this patent is extended or adjusted under 35 U.S.C. 154(b) by 361 days.

(21) Appl. No.: 12/163,031

(22) Filed: Jun. 27, 2008

(65) Prior Publication Data

US 2009/0326307 A1    Dec. 31, 2009

(51) Int. Cl.
*F25J 3/00* (2006.01)
*C07C 7/04* (2006.01)

(52) U.S. Cl. ............................ 585/809; 585/802; 62/620

(58) Field of Classification Search .................. None
See application file for complete search history.

(56) References Cited

U.S. PATENT DOCUMENTS

| | | | | |
|---|---|---|---|---|
| 3,002,358 | A | * 10/1961 | Dierl | 62/630 |
| 3,568,457 | A | * 3/1971 | Briggs et al. | 62/620 |
| 4,336,046 | A | * 6/1982 | Schorre et al. | 62/623 |
| 4,559,108 | A | * 12/1985 | Ahlberg | 202/154 |
| 4,753,667 | A |   6/1988 | O'Connell et al. | |
| 5,973,171 | A |  10/1999 | Cochran | |
| 6,218,589 | B1 |   4/2001 | Cottrell | |

OTHER PUBLICATIONS

U.S Department of Energy; Industrial Technologies Program, Industrial Heat Pumps for Steam and Fuel Savings [Online], Jun. 1, 2003, pp. 1-17, 17 pages.*
Mauhar et al. "Optimization of Propylene—Propane Distillation Process," Chemical Papers, 2004, vol. 58, No. 6, pp. 386-390, 4 pages.*
PCT International Search Report and Written Opinion issued in International Application No. PCT/US09/48220, dated Nov. 6, 2009, 9 pages.
U.S. Department of Energy: Industrial Technologies Program, "Industrial Heat Pumps for Steam and Fuel Savings"[online], Jun. 1, 2003, from http://www1.eere.energy.gov/industry/bestpractices/pdfs/heatpump.pdf; p. 4, para. 4, 2 pages.
Mauhar et al. "Optimization of Propylene—Propane Distillation Process," Chemical Papers, 2004, vol. 58, No. 6, pp. 386-390, 4 pages.

* cited by examiner

*Primary Examiner*—Tam M Nguyen
(74) *Attorney, Agent, or Firm*—Osha • Liang LLP

(57) ABSTRACT

Improved processes for the separation of olefins from paraffins, such as propylene from propane are provided. Two product splitters are used in parallel to separate propylene from propane. One of the product splitters operates at a lower pressure, while the second product splitter operates at a higher pressure. The use of the two splitters in parallel provides a process for recovery of a high purity propylene product with lower energy consumption compared to prior art processes.

17 Claims, 3 Drawing Sheets

SEPARATION PROCESS FOR OLEFIN PRODUCTION

FIELD OF THE INVENTION

The present invention is directed to an improved process for the production of olefins, and in particular for the separation of olefins produced by a dehydrogenation process from paraffin feed stocks. The process is particularly suited to separation of propylene and propane. Two product splitters are used in parallel to separate propylene from propane to produce a high purity propylene product. One of the product splitters is used at a lower pressure, while the second splitter is operated at a higher pressure. The use of the two splitters in parallel provides a process for recovery of a high purity propylene product with lower energy consumption compared to prior art processes.

BACKGROUND

Olefin hydrocarbons are useful for the production of a number of petrochemical products, such as polymers, motor fuel blending additives, and other products. Short chain saturated hydrocarbons having from 2 to 5 carbon atoms per molecule are often subjected to dehydrogenation to form the corresponding olefin. The olefins, in turn, may be used in the alkylation of isoparaffins, in the etherification of alcohols to make motor fuel blending additives, or as monomers used to produce various polymer materials.

One particularly useful olefin is propylene, which is produced by dehydrogenation of propane. Propylene is the world's second largest petrochemical commodity and is used in the production of polypropylene, acrylonitrile, acrylic acid, acrolein, propylene oxide and glycols, plasticizer oxo alcohols, cumene, isopropyl alcohol and acetone. The growth in propylene production is primarily driven by the industry demand for polypropylene, which is used in such everyday products as packaging materials and outdoor clothing.

Propane dehydrogenation processes generally follow the steps shown in FIG. 1. Propane is fed to a dehydrogenation unit (1) where dehydrogenation is performed in the presence of a catalyst to form propylene. The effluent from the dehydrogenation unit is compressed in a compressor (2) to a sufficiently high pressure, typically 115 to 350 psig or greater, to recover unreacted propane and propylene from lighter components in a recovery section.

In the recovery section (3), the compressed reactor effluent is successively chilled with refrigeration to maximize the recovery of propane and propylene for further purification. The offgas from the recovery section consists mainly of lighter components, such as hydrogen, methane, ethane and ethylene.

The hydrocarbon product stream is fed from the recovery unit to a purification unit (4). The purification unit typically comprises two distillation columns. In the first distillation column, a deethanizer, ethane and lighter components are recovered as overhead offgas and propane and propylene are removed as bottoms.

The bottoms stream from the deethanizer is then fed to a second distillation column typically referred to as a product splitter. In the product splitter column, propylene is recovered as an overhead stream and unreacted propane from the bottoms stream of the product splitter is recycled back to the dehydrogenation unit.

In the conventional process, the product splitter is typically reboiled using a heat pump configuration in which the overhead product vapor from the product splitter is compressed and used as the reboiling medium. While it is possible to increase the pressure in the product splitter and reboil using low pressure steam, the propane dehydrogenation unit typically does not produce enough low level steam to reboil a high pressure product splitter.

One common process for production of propylene by dehydrogenation of propane is known as the CATOFIN process. In the CATOFIN process, propane is converted to propylene by feeding liquid propane to a dehydrogenation reactor containing a fixed bed Chromium-Alumina catalyst. There are typically multiple dehydrogenation reactors operating in parallel to allow catalyst regeneration to occur in some reactors while others are in operation. The dehydrogenation reactors are typically maintained at about 690° F.

The effluent from the reactors is cooled and compressed using a steam driven product compressor. The compressed product is sent to a recovery section where inert gases, hydrogen and light hydrocarbons are removed from the compressed reactor effluent. The propylene rich gas from the recovery unit is then sent to the product purification section where propylene is separated from propane as described above.

The purification step of a conventional propane dehydrogenation process is shown in FIG. 2. The product splitter (110) in the conventional process is fed the heavy end from a deethanizer which contains C3+ compounds through feed line (100). This feed is distilled in the product splitter such that the propylene product is recovered in the overhead stream (102) and the majority of the remaining compounds, including unreacted propane, exit in the bottoms stream (104). This conventional product splitter is operated at pressures of about 80-90 psig and temperatures of 40 to 60° F.

The overhead propylene stream (102) is combined with the overhead (105) from separator (150) and sent to heat pump (130) through line (106). The heat pump is driven by steam turbine (131) using high pressure steam provided through line (133). The exhaust steam is discharged through line (122) to condenser (160), where it is cooled and discharged from the plant.

The product is compressed in heat pump (130) and flows through discharge line (108) to provide heat to product splitter reboiler (120). The warmed propylene is split, with a portion flowing back to the product splitter through line (114), and the remainder flowing through line (112) to product separator (150). The overhead (105) from the separator (150) is combined with the overhead propylene stream (102) from the product splitter and fed to the heat pump (130) as described above. The propylene product (118) from the bottoms of the separator is sent to other units for further processing.

The product compression machine (140) is driven by steam turbine (141) which is fed high pressure steam through line (143). The product compressor is fed the product from the dehydrogenation reactor (not shown) through line (127) for compression. The compressed dehydrogenation product is fed through line (126) for further separation. In conventional plants, the exhaust steam from the steam turbine (141) is discharged through line (124) to condenser (170), where it is cooled and discharged from the plant.

The bottoms of the conventional low pressure product splitter is comprised mainly of propane. The bottoms are discharged through line (128) and split, with a portion of the bottoms recycled through line (104) to reboiler (120), where it is heated and sent back to the low pressure splitter (11) to provide heat. The remainder of the bottoms are discharged through line (116) and sent for further processing.

Conventional dehydrogenation processes, however, have some inherent limitations. One primary limitation is the amount of input energy required to produce the propylene product. Currently, the total energy consumption for the conventional dehydrogenation process is about 100 kcal/kg of propylene product. As such, there exists an ongoing and unmet need in the industry for a less expensive and more energy efficient method for dehydrogenation of propane.

SUMMARY OF THE INVENTION

The present invention relates to processes for separating olefins from paraffin feedstocks. The process may be used for example for separating propylene from propane following a dehydrogenation process to produce propylene from propane. The process uses two product splitters in parallel, a first splitter operated at a higher pressure and a second splitter operated at a lower pressure. The low pressure product splitter has a reboiler that has heat supplied using a heat pump as is typically done in conventional propylene purification processes. The high pressure product splitter operates at a higher pressure and has a reboiler that has heat supplied using exhaust steam from the steam turbines of the product compressor and the heat pump.

In one embodiment of the invention, a feed stream comprised of a mixture of propylene and propane is split into two streams. The first stream is fed to a high pressure product splitter column and the second stream is fed to a low pressure product splitter column. At least a portion of the overhead stream from the low pressure product splitter column is fed to a heat pump. Exhaust steam from the steam turbine which drives the heat pump is fed to the reboiler for the high pressure product splitter.

The heat pump may be used to compress the overhead stream from the low pressure product splitter column. In some embodiments of the invention, the compressed overhead stream from the low pressure product splitter is fed through the reboiler for the low pressure product splitter column.

One or more product compressors are used to compress the output from the dehydrogenation reactors that convert the paraffin feed to an olefin product. The product compressor is driven by a steam turbine. The exhaust steam from the steam turbine for the product compressors may be combined with the exhaust steam from the steam turbine from the heat pump and the combined stream is used to provide heat to the reboiler for the high pressure product splitter.

In another embodiment of the invention, the overhead streams from the product splitter columns are split into reflux streams and product streams. The reflux streams are fed back to the respective product splitter columns, and the product streams are fed to other units for further processing.

In yet another embodiment of the invention, a separator is provided. The compressed overhead stream from the low pressure product splitter column is fed to the separator after providing heat to the reboiler for the low pressure product splitter. The overhead stream from the separator is combined with the overhead stream from the low pressure product splitter column, and the bottoms stream from the separator containing the propylene product is sent to other units.

The feed stream to the parallel product splitters may be provided from any type of plant that is capable of converting a paraffin to an olefin, such as propane to propylene, and utilizes a separation stage to separate unreacted propane from propylene. Propylene may be produced for the process of the present invention using any type of dehydrogenation process to convert propane to propylene, such as for example the CATOFIN process. In a preferred embodiment, the product stream from the dehydrogenation unit is further treated, such as by compression and refrigeration, to remove inert gases, hydrogen and light hydrocarbons. The product stream is preferably fed to a deethanizer column, in which $C_2$ and lighter components are removed in an overhead stream and the bottoms stream is composed of propane and propylene with a small quantity of other impurities. In this embodiment, the deethanizer bottoms stream is fed to the parallel product splitter stage of the present invention.

The product purification stage generally comprises the low pressure product splitter, the high pressure product splitter, a steam turbine driven heat pump, and a steam turbine driven product compressor. The deethanizer bottoms stream enters the product purification stage and is split such that the reboiler steam requirement for the high pressure splitter is met by the exhaust steam from the steam turbines that drive the product compressor and the heat pump. Heat for the reboiler for the low pressure product splitter is provided from the heat pump as in conventional product splitter arrangements.

The separation process described may be used in any olefin conversion process to separate an olefin from a feed stock such as a paraffin. The process of the present invention is particularly advantageous for processes that require a considerable amount of power provided by a steam turbine or that requires energy intensive separation because the products have a small differential in boiling temperature.

Among the advantages of the process of the present invention is that high purity propylene can be produced with lower total energy consumption. For example, total energy consumption using the product purification scheme of the present invention may reduce the total energy consumption by as much as about 18-22% as compared to conventional CATOFIN units. Other advantages of the processes of the invention will be apparent to those skilled in the art based upon the following detailed description of preferred embodiments.

DETAILED DESCRIPTION OF PREFERRED EMBODIMENTS

The present invention relates to improved processes for energy intensive separations, such as in the production of propylene from propane. In the processes of the present invention, feed from a process for conversion of paraffins to olefins, such as the bottoms from a deethanizer column, is split and fed to two product splitter columns operating in parallel. One product splitter column operates at a higher pressure, while the second product splitter operates at a lower pressure.

Figure 1:
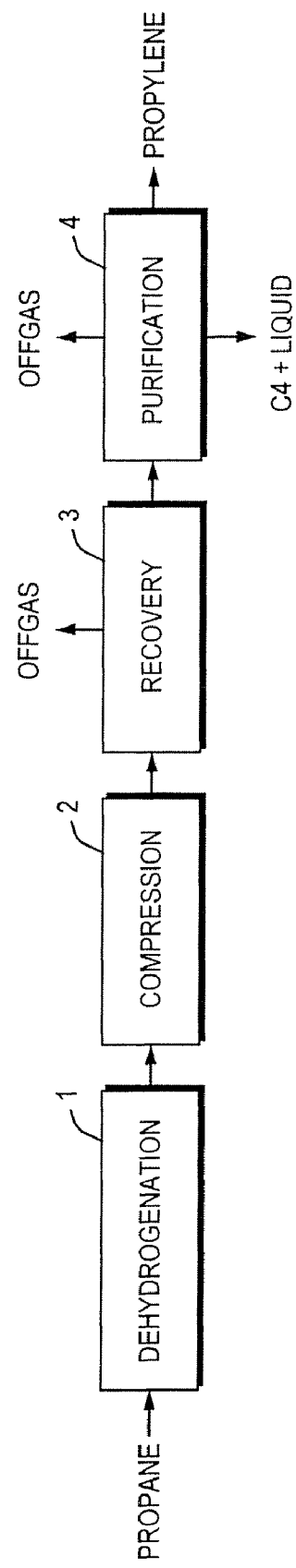
FIG. 1 shows the steps of a conventional process for production of polypropylene from propane.
Figure 2:
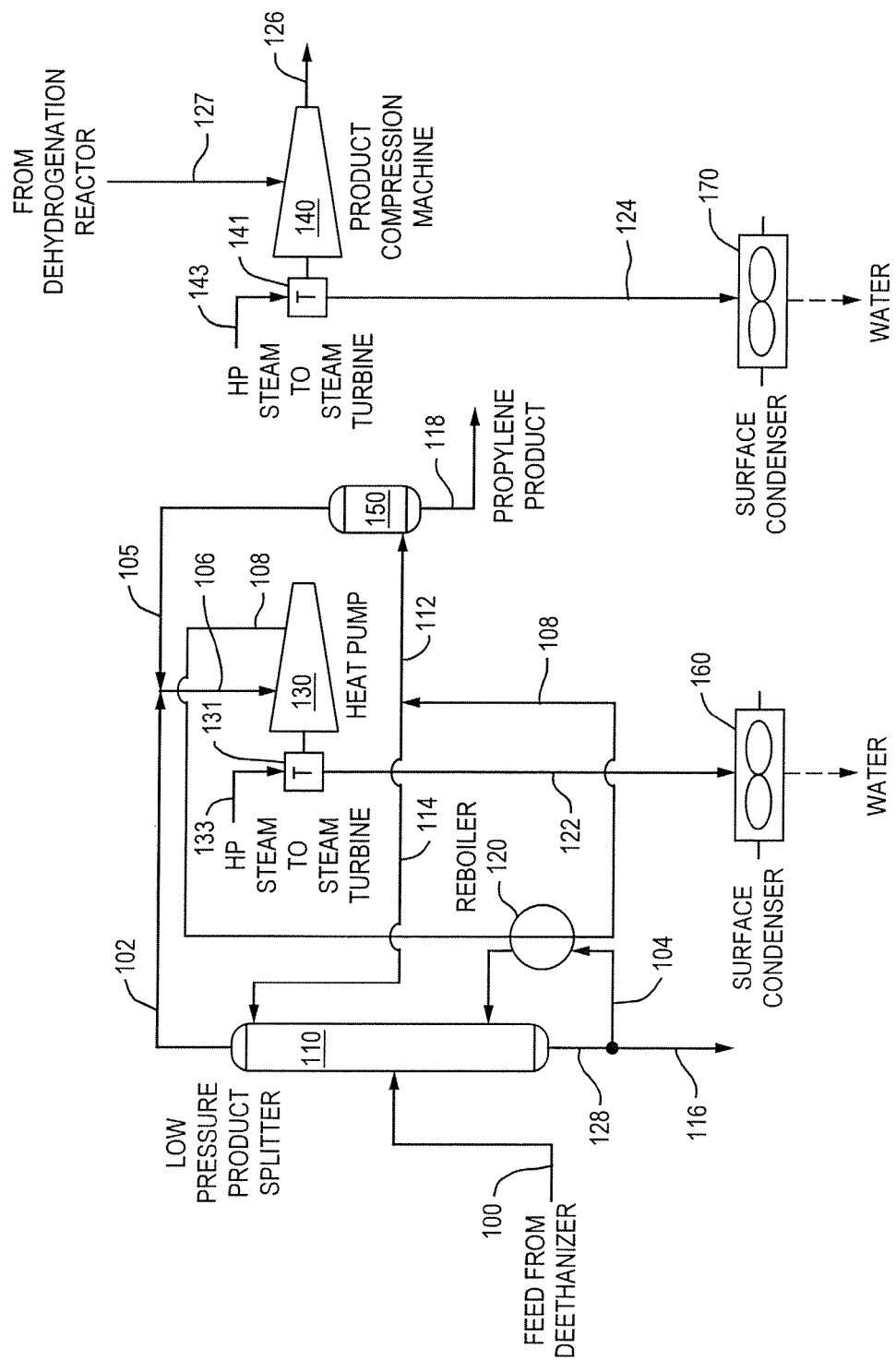
FIG. 2 shows a detailed schematic of a conventional prior art processing scheme.

In the processes of the present invention, a product stream is obtained from an olefin conversion plant, such as a dehydrogenation unit. In one embodiment, propane may be fed to any type of conventional dehydrogenation unit to produce propylene. As shown in FIG. 1, typically the dehydrogenation unit product stream is compressed and sent to a recovery unit to remove inert gases, hydrogen and other lighter components to maximize recovery of propane and propylene. The product stream is then sent from the recovery unit to a deethanizer column where $C_2$ and lighter components are removed as overhead vapors. In a preferred embodiment, the dehydrogenation units are CATOFIN type reactors.

The following description of preferred embodiments of the present invention are provided as exemplary only, and are not intended to limit the full scope of the invention described and claimed herein in any way. It should be understood that the processes described below may be used in any olefin conversion process to separate an olefin from a feed stock such as a paraffin. In particular, the process may be used for separations that require a considerable amount of power provided by a steam turbine or that requires energy intensive separation because the products have a small differential in boiling temperature.

Figure 3:
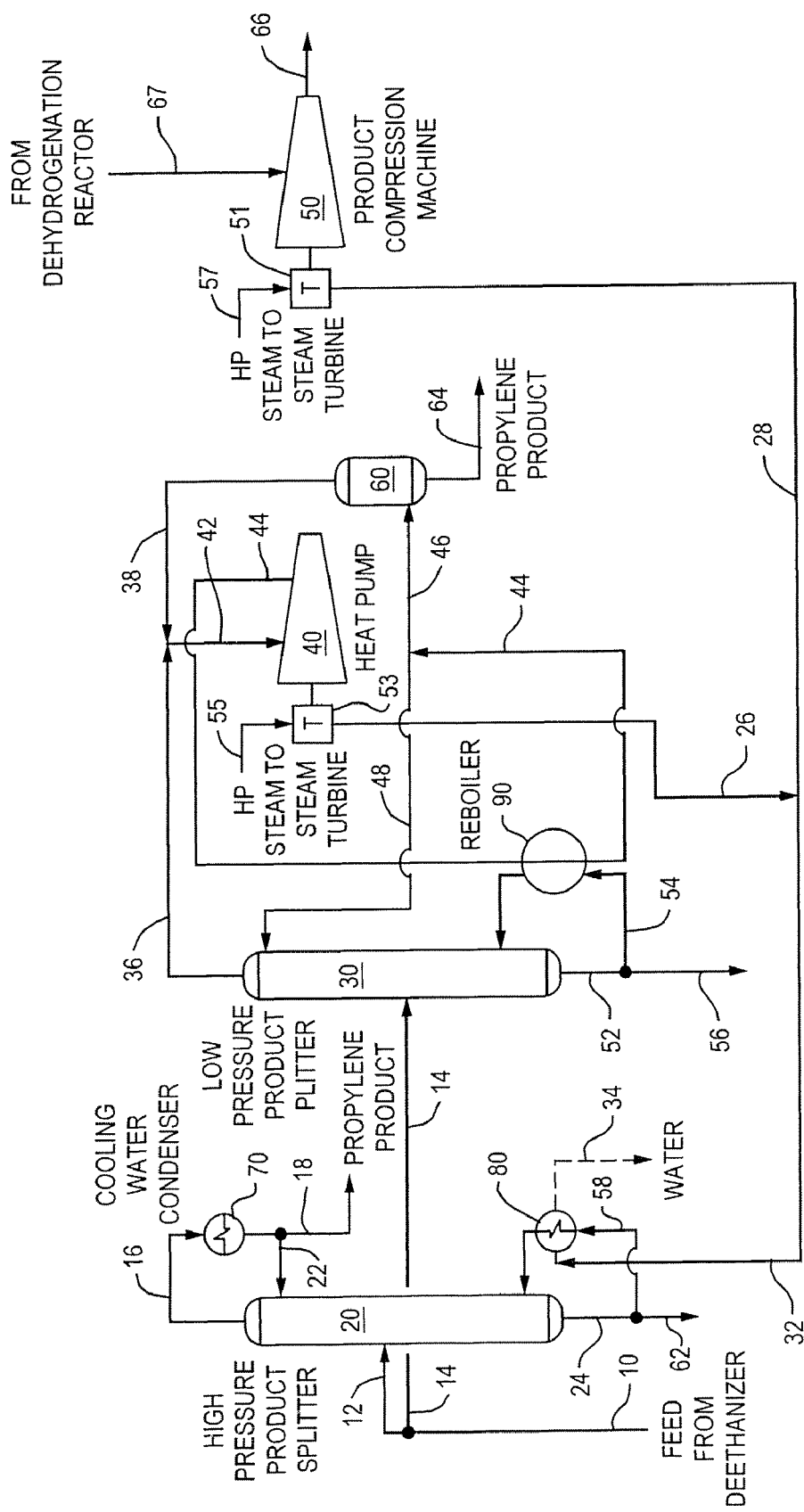
FIG. 3 is a schematic drawing of a process for production of polypropylene from propane using a low pressure splitter and a high pressure splitter in parallel.

A schematic of an embodiment of the present invention for separating propane and propylene is shown in FIG. 3. The bottoms from a deethanizer column are fed to the parallel low and high pressure product splitters for purification of the propylene product. As shown in FIG. 3, the bottoms from the deethanizer are fed through line (10) and are split into two separate feed lines (12, 14) for the two product splitters. It is to be understood that the flow rate from the deethanizer to the product splitters is selected and controlled based upon the size of the product splitters and to maximize the efficiency and operation of the plant. Preferably, about 10% to 35% of the feed from the deethanizer is fed to the low pressure column (30), with the remainder being fed to the high pressure column (20).

A first feed line (12) feeds the deethanizer bottoms to the high pressure product splitter (20). A second feed line (14) feeds the low pressure product splitter (30). The feed from the deethanizer is split between the first and second feed lines such that the feed to the high pressure product splitter is at a flow rate that can be processed using exhaust steam from the steam turbine used to drive the product compressor (50) and the heat pump (40) as described below.

The high pressure product splitter (20) operates at a pressure between about 170 psig and 350 psig, and preferably operates at a pressure of about 275 psig. The feed stream (12) from the deethanizer is fed to the high pressure product splitter (20) in which propane is separated from propylene. The high pressure product splitter is a distillation column of a typical design used for separation of propane and propylene. The purified propylene product exits the high pressure splitter through overhead line (16) and is fed through a condenser (70) that is cooled with water. Preferably, the cooling water is supplied to the condenser at a temperature and flow rate sufficient to provide the necessary cooling to cool the propylene product to the desired temperature. The propylene product is liquified in the condenser and a portion of the product stream is split and fed through reflux line (22) to the high pressure product splitter (20). The remaining propylene product is fed through line (18) to storage or to another unit for further processing. The propylene product stream preferably exits the condenser at a temperature of between about 85° F. and 105° F.

Propane is removed from the bottom of the high pressure product splitter (20) through line (24). A portion of the bottoms is fed through line (58) through reboiler (80) and back into the high pressure product splitter. The recirculated bottoms is heated in the reboiler to a temperature of between about 110° F. and 140° F. Heat is provided to the reboiler through steam line (32), which is supplied from the exhaust steam line (26) from the steam turbine (55) of heat pump (40) and the exhaust steam line (28) from the steam turbine (51) of the product compressor (50). Condensed water and cooled steam is discharged from the reboiler through line (34). The remainder of the propane that is not recycled is removed through line (62) for further processing. Typically, the propane will be recycled and fed to the dehydrogenation unit. Preferably, the split between the propane fed to the reboiler and the recycled propane is between about 20/1 and 40/1.

The low pressure product splitter (30) operates at a pressure of between about 60 psig and 100 psig, and preferably operates at a pressure of about 75 psig. The feed stream (14) from the deethanizer is fed to the low pressure product splitter (30) in which propane is separated from propylene. The purified propylene product exits the low pressure product splitter through overhead line (36). The propylene product is combined with overhead from separator (60) fed through line (38), and the combined stream is fed through line (42) to heat pump (40). Preferably, the propylene product stream is compressed in the heat pump to a pressure of between about 150 psig and 290 psig at a temperature of between about 110° F. and 150° F. The heat pump (40) is driven by steam turbine (53). High pressure steam, preferably at about 600 psig to 650 psig, is fed to the steam turbine (53) to drive the heat pump (40). The exhaust from the steam turbine (53) is fed through line (26) and combined with exhaust steam in line (28) to feed the high pressure splitter reboiler (80) as described above.

The compressed propylene exits heat pump (40) through line (44), and is fed through low pressure splitter reboiler (90) to provide heat for the reboiler. In the reboiler (90), the compressed propylene is cooled to a temperature of between about 75° F. and 100° F. After cooling in the reboiler, the propylene product is split. A portion of the propylene product is fed through line (48) as reflux for the low pressure product splitter (30). The majority of the propylene product stream is fed to separator (60) through line (46). Preferably, the split between reflux propylene and the product propylene is between about 10/1 and 20/1. Propylene product is removed from the separator (60) through product line (64) and fed to storage or to other units for further processing.

Propane is removed from the bottom of the low pressure product splitter through bottoms line (52). A portion of the bottoms are split and fed through line (54) to reboiler (90), where the stream is heated and fed at the bottom of the product splitter (30). The remainder of the propane is removed through line (56) for processing. Preferably, the split between the propane fed to the reboiler and the recycled propane is about $^1/_{10}$ and $^4/_{10}$. Typically, the propane is recycled to the dehydrogenation unit for further processing.

The product compressor (50) provides compression for the output from the dehydrogenation reactors (not shown). The output from the dehydrogenation reactors is fed to the product compressor through line (67), and the compressed product is fed through line (66) for processing and separation. The product compression machine is driven by steam turbine (51). High pressure steam, preferably at about 600 psig to 650 psig, is supplied through line (57) to the steam turbine (51) to drive the product compressor (50). The exhaust from the steam turbine (51) is fed through line (28) to the high pressure splitter reboiler (80) as described above. Preferably, the dehydrogenation reactor product stream exits the product compression machine through line (66) at a pressure of about 150 psig or greater, and at a temperature of between about 230° F. and 250° F. Preferably, the propylene product stream comprises at least 30% propylene.

The process described above provides a more energy efficient means of separating propane from propylene to obtain a high purity propylene product. The exhaust steam from the steam turbines for the heat pump and product compressor is used to supply heat to the reboiler for the high pressure splitter, thereby recovering and using energy that had previously been lost. For example, the process of the present invention uses 78-82 Kcal/kg of propylene product, an improvement of 18-22% over conventional CATOFIN processes.

While preferred embodiments have been shown and described, various modifications may be made to the processes described above without departing from the spirit and scope of the invention as described in the appended claims. For example, the process described above may be used in any olefin conversion process that requires a considerable amount of power provided by a steam turbine or requires energy intensive separation because the products have a small temperature differential. Accordingly, it is to be understood that the present invention has been described by way of example and not by limitation.

The invention claimed is:

1. A process for separation of an olefin from a paraffin in a product stream from a dehydrogenation system, comprising the steps of:
   (a) supplying a feed stream substantially comprised of a mixture of at least one olefin and at least one paraffin;
   (b) splitting the feed stream into a first portion and a second portion;
   (c) feeding the first portion of the feed stream to a first product splitter column and feeding the second portion of the feed stream to a second product splitter column, wherein the first product splitter column is operated at a higher pressure than the second product splitter column;
   (d) feeding at least a portion of the overhead stream from the second product splitter column to a heat pump to compress the second product splitter overhead stream; and
   (e) feeding steam from at least one steam turbine which drives the heat pump to the reboiler for the first product splitter column.

2. The process of claim 1, further comprising the steps of:
   (f) flowing the compressed second product splitter overhead stream from the heat pump through a reboiler for the second product splitter.

3. The process of claim 2, further comprising the steps of:
   (g) feeding steam from at least one steam turbine which drives the product compressor to a reboiler for the first product splitter column.

4. The process of claim 3, further comprising the steps of:
   (i) splitting the overhead stream from the first product splitter into a reflux stream which is fed back to the first product splitter and a product stream; and
   (j) splitting the compressed second product splitter overhead stream from the heat pump into a reflux stream which is fed back to the second product splitter and a product stream.

5. The process of claim 2, further comprising the steps of:
   (g) feeding the compressed second product splitter overhead stream from the reboiler for the second product splitter to a separator to separate the second product splitter overhead stream into a separator bottoms stream comprising propylene product and a separator overheads stream; and
   (h) combining the separator overhead stream with the overhead stream from the second product splitter and feeding the combined stream to the steam turbine driven heat pump.

6. The process of claim 1, wherein the first product splitter column is operated at a pressure of between about 170 psig and 350 psig, and the second product splitter column is operated at a pressure of between about 60 psig and 100 psig.

7. The process of claim 6, wherein the olefin is propylene and the paraffin is propane.

8. The process of claim 1, wherein the first product splitter column is operated at a pressure of between about 275 psig, and the second product splitter column is operated at a pressure of between about 75 psig.

9. The process of claim 7, wherein between about 65% and 90% of the feed stream is contained in the first portion of the feed stream.

10. A process for separation of an olefin from a paraffin in a product stream from a dehydrogenation system, comprising the steps of:
    (a) supplying a feed stream substantially comprised of a mixture of at least one olefin and at least one paraffin;
    (b) splitting the feed stream into a first portion and a second portion;
    (c) feeding the first portion of the feed stream to a first product splitter column and feeding the second portion of the feed stream to a second product splitter column, wherein the first product splitter column is operated at a higher pressure than the second product splitter column;
    (d) feeding the overhead stream from the second product splitter column to a heat pump to compress the second product splitter overhead stream;
    (f) flowing the compressed second product splitter overhead stream from the heat pump through a reboiler for the second product splitter;
    (g) splitting the compressed second product splitter overhead stream into a reflux stream which is fed back to the second product splitter and a product stream;
    (h) splitting the overhead stream from the first product splitter into a reflux stream which is fed back to the first product splitter and a product stream; and
    (i) combining the steam from at least one steam turbine which drives a dehydrogenation reactor output compressor and steam from at least one steam turbine which drives the heat pump, and feeding the steam to the reboiler for the first product splitter column.

11. The process of claim 10, further comprising the steps of:
    (j) feeding the product stream of step (g) to a separator and separating the product stream into a separator bottoms stream comprising propylene product and a separator overheads stream; and
    (k) combining the separator overhead stream with the overhead stream from the second product splitter and feeding the combined stream to the steam turbine driven heat pump.

12. The process of claim 10, wherein the olefin is propylene and the paraffin is propane.

13. The process of claim 10, wherein the first product splitter column is operated at a pressure of between about 170 psig and 350 psig, and the second product splitter column is operated at a pressure of between about 60 psig and 100 psig.

14. The process of claim 10, wherein the first product splitter column is operated at a pressure of between about 275 psig, and the second product splitter column is operated at a pressure of between about 75 psig.

15. The process of claim 13, wherein between about 65% and 90% of the feed stream is contained in the first portion of the feed stream.

16. The process of claim 11, wherein the first product splitter column is operated at a pressure of between about 170 psig and 350 psig, and the second product splitter column is operated at a pressure of between about 60 psig and 100 psig.

17. The process of claim 16, wherein the olefin is propylene and the paraffin is propane.

* * * * *